United States Patent
Dudzinski et al.

(10) Patent No.: US 10,014,079 B2
(45) Date of Patent: Jul. 3, 2018

(54) BUSINESS METHOD FOR COLLECTION, PROCESSING, CRYOGENIC STORAGE AND DISTRIBUTION OF A BIOLOGIC SAMPLE MATERIAL

(75) Inventors: Anthony Dudzinski, Middletown, NJ (US); Christopher J. Neill, New Brunswick, NJ (US); John S. Arnone, Shrewsbury, NJ (US)

(73) Assignee: American Cryostem Corporation, Eatontown, NJ (US)

( * ) Notice: Subject to any disclaimer, the term of this patent is extended or adjusted under 35 U.S.C. 154(b) by 713 days.

(21) Appl. No.: 13/702,304

(22) PCT Filed: Jun. 6, 2011

(86) PCT No.: PCT/US2011/039260
§ 371 (c)(1),
(2), (4) Date: Jun. 30, 2013

(87) PCT Pub. No.: WO2011/156267
PCT Pub. Date: Dec. 15, 2011

(65) Prior Publication Data
US 2013/0325492 A1    Dec. 5, 2013

Related U.S. Application Data

(60) Provisional application No. 61/352,217, filed on Jun. 7, 2010.

(51) Int. Cl.
*G16H 10/40* (2018.01)
*G06Q 10/08* (2012.01)
*G16H 40/63* (2018.01)
*G06Q 30/02* (2012.01)
*G06Q 50/22* (2018.01)

(52) U.S. Cl.
CPC .......... *G16H 40/63* (2018.01); *G06Q 10/08* (2013.01); *G06Q 30/0283* (2013.01); *G06Q 50/22* (2013.01); *G16H 10/40* (2018.01)

(58) Field of Classification Search
CPC ........ G06Q 50/22; G06Q 50/24; G06Q 10/08; G06Q 30/0283; G16H 10/40
USPC ...................................................... 705/2–3
See application file for complete search history.

(56) References Cited

U.S. PATENT DOCUMENTS

| | | | |
|---|---|---|---|
| 9,255,664 B2* | 2/2016 | Gerstler | F17C 9/04 |
| 2004/0085443 A1* | 5/2004 | Kallioniemi | G01N 1/36 348/135 |
| 2007/0179717 A1* | 8/2007 | Milliken | G01N 1/42 702/31 |
| 2008/0064098 A1* | 3/2008 | Allickson | C12N 5/0605 435/366 |
| 2008/0219885 A1* | 9/2008 | Horstman | A61B 10/0096 422/400 |
| 2008/0227210 A1* | 9/2008 | Smith | A61B 10/0051 436/86 |
| 2009/0023128 A1* | 1/2009 | Zimmermann | A01N 1/02 435/1.3 |

* cited by examiner

*Primary Examiner* — Eliza A Lam

(57) ABSTRACT

Methods and systems for collection, processing, cryogenic storage and distribution of a stem cell based biological sample material.

4 Claims, 2 Drawing Sheets

BUSINESS METHOD FOR COLLECTION, PROCESSING, CRYOGENIC STORAGE AND DISTRIBUTION OF A BIOLOGIC SAMPLE MATERIAL

CROSS REFERENCE TO RELATED APPLICATIONS

This application claims priority to U.S. Provisional Application No. 61/352,217 filed Jun. 7, 2010, incorporated herein in its entirety.

FIELD OF THE INVENTION

The invention is directed to a business method for collection, processing, cryogenic storage and distribution of a biological sample material.

BACKGROUND OF THE INVENTION

The business of collecting, processing, and long term storage of biological samples allows healthy individuals to privately preserve their tissue for future use in therapy. Individualized collection and storage provides a solution to and for "personalized medicine" issues or as "bioinsurance" by making the patient's own preserved tissue available for future use.

Business methods which are established for this reason are not only required to coordinate a unique process for the specific tissue for preservation, but also include equipment to complement the process to accomplish this objective. In addition, successful methods also need to appreciate and include other services to effectively and efficiently obtain a substantially pure and viable cryogenically stored sample for later use.

Recent developments in the understanding and properties of tissues and cells allow for advancement in science wherein biological samples obtained can be processed and cryogenically stored for later use for a variety of therapies. However, though the science may exist, a cost effective, dependable and long-term business method must also exist to make this idea viable.

BRIEF SUMMARY OF THE INVENTION

In a first embodiment, the invention is directed to a business method for collection, processing, cryogenic storage and distribution of a biological sample material. The method includes the steps of collecting a premium for defined services for collection, cryogenic storage and distribution of a biological sample material. Upon receipt of the premium coordinating the collection of a biological sample of a client includes, (i) paying a predetermined fee in support of physician services performed for collection of the biological sample and (ii) supplying a collection system including a plurality of components for collection and transportation of the biological sample. The method continues by obtaining the biological sample from the client and transporting the biological sample in the collection system to a processing facility. The collection system components are introduced to a processing module of a database via a log-in port. The biological sample is processed to disassociate, separate and isolate material for cryopreservation. Testing is performed for quality control of the isolated material for cryopreservation and thereafter the isolated material is cryopreserved. The method continues by selecting outside facilities for storage of the isolated cryopreserved material and storing the cryopreserved isolated material. The calculating of storage fees occurs for distribution of the isolated material to at least one (1) of, (i) client from which the biological sample was obtained, (ii) research group or (iii) entity from which biological sample was not obtained.

In another embodiment, the invention is directed to a method for collection, processing, cryogenic storage and distribution of an autologous stem cell biological sample material derived from adipose tissue. The method includes the steps of collecting a premium for defined services for collection, transportation, cryogenic storage and distribution of an autologous stem cell biological sample material derived from adipose tissue, and thereafter coordinating the collection of the autologous stem cell biological sample material derived from adipose tissue of a client including (i) paying a predetermined fee in support of physician services performed for collection of the biological sample, and (ii) supplying a collection system including a plurality of components for collection and transportation of the biological sample. The autologous stem cell biological sample material derived from adipose tissue is obtained by various removal techniques from the client and transferred to a defined container having at least one port. The method continues by transporting the autologous stem cell biological sample material derived from adipose tissue in the collection system to a processing facility and introducing information from the collection system components to a processing module of a customized database. The autologous stem cell biological sample material derived from adipose tissue is processed, wherein the autologous stem cell biological sample material derived from adipose tissue is disassociated to separate and isolate material for cryopreservation. Testing for quality control of the autologous isolated material for cryopreservation is performed prior to cryopreserving the autologous isolated material. Facilities for storage of the autologous isolated cryopreserved material are selected and thereafter, the cryopreserved autologous isolated materials in the selected facility are stored. Storage fees are calculated for distributing the cryopreserved isolated material designated by a client.

In another embodiment, the invention is directed to a system for collection, cryogenic storage and distribution of a biological sample. The system includes a collection system and a collection system transportation system to a processing facility, having access to a database. A first portable storage facility and a first portable storage facility transportation system allow transport to a second storage facility. The system further includes a retrieval system for calculating storage fees for distributing the isolated material to at least one of (i) customer from which biological sample was obtained, (ii) research group; (iii) customer from which biological sample was not obtained.

In yet another embodiment, the invention is directed to an interactive system for collection, cryogenic storage and distribution of a biological sample including at least three interactive modules. The organization or processing module is able to organize collection and storage of information from a client module, most commonly a patient, for obtaining and processing a biological material. A provider module, is capable to extract the biological material from the client module and initiate transport of the extracted biological sample to the processing module for processing.

DETAILED DESCRIPTION OF THE INVENTION

Figure 1:
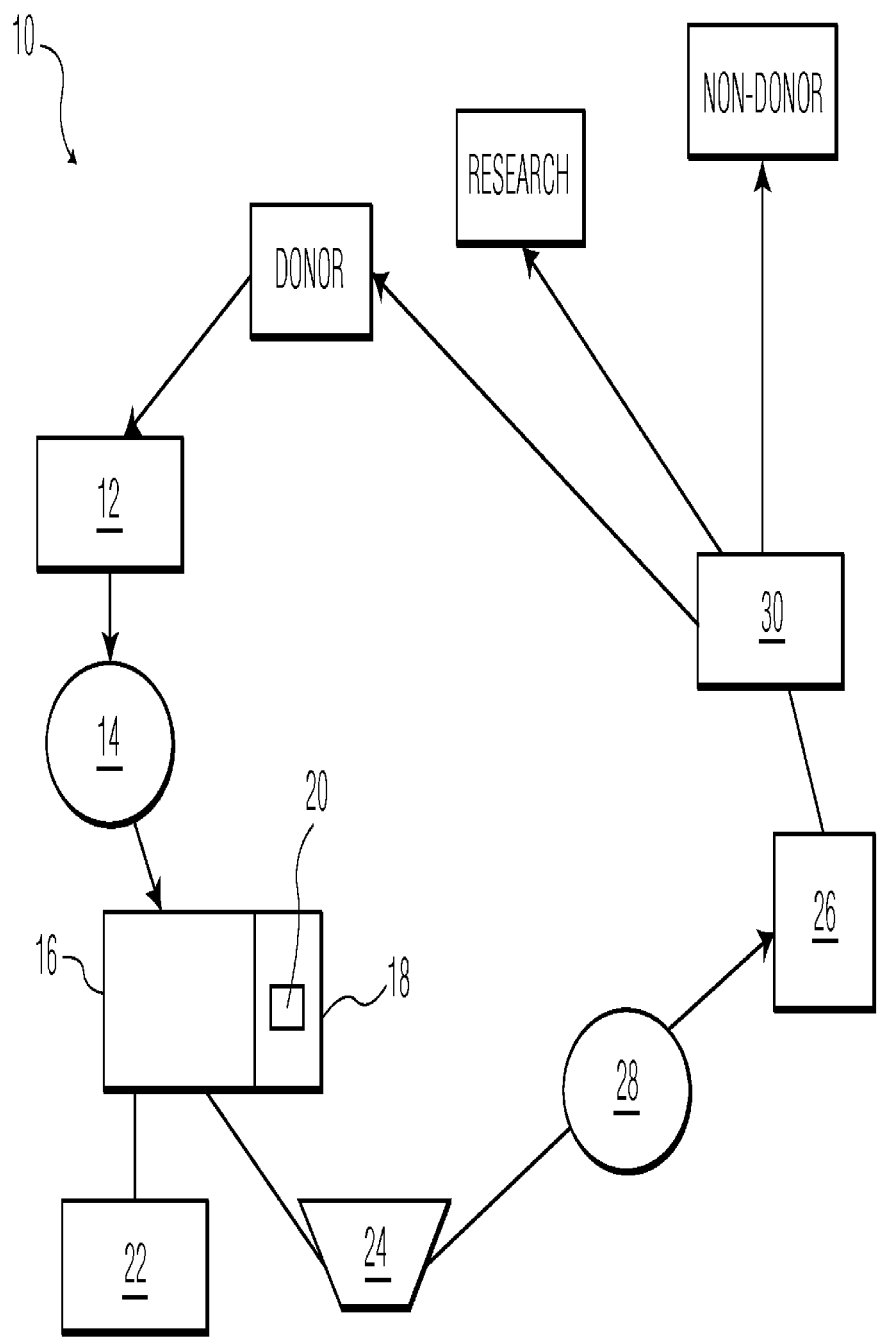
FIG. 1 is a schematic view of the system of the present invention.

Certain terminology is used herein for convenience only and is not to be taken as a limitation on the present invention. The terminology includes the words specifically mentioned, derivatives thereof and words of similar import. The embodiments discussed herein are not intended to be exhaustive or to limit the invention to the precise form disclosed. These embodiments are chosen and described to best explain the principle of the invention and its application and practical use and to enable others skilled in the art to best utilize the invention. As recognized herein, the terms "physician", "provider" and "practitioner" are used to represent the same entity and have the same meaning herein. Other multiple terms are used to represent the same meaning as defined herein.

In a first embodiment, the invention is directed to a business method for collection, processing, cryogenic storage and distribution of a biological sample material by a business method. The method is initiated by collecting a premium for defined services for collection, cryogenic storage and distribution of a biological sample material and thereafter, coordinating the collection of a biological sample of a client by (i) paying a predetermined fee in support of physician services performed for collection of the biological sample, and (ii) supplying a collection system including a plurality of components for collection and transportation of the biological sample. Most commonly this occurs via a web-based system allowing access by physicians/medical providers, the business entity and clients so as to allow review of documents and status updates of the biological sample and isolated material as defined herein.

This initial part of the business method is of core importance not only to obtain the sample but to initiate the business relationship of the client and business entity. The client, physician and business entity will gain an understanding of the "big picture" and long-term relationship of this collaboration so as to appreciate the benefits, rights, obligations and costs (as explained herein). Most commonly, the physician has been established (enrolled) in a network of physicians for the business entity. The physician has been educated on the process included in the business method including information of the business entity objectives, services and products; in addition to "best practices" to obtain an uncontaminated sample. The physician will request a collection system from the business entity via a business entity website (as discussed herein). The business entity "laboratory" or "processing facility" will assemble and ship the collection system to the physician with the appropriately labeled bags and documents according to standard procedures established by the business entity. The collection system must be visually inspected upon receipt by the physician and an inspection checklist will be included for reference. The physician will complete, or have staff complete, all requested information on the pre-labeled forms prior to the creation of an aseptic environment for collection of the sample. The physician will thereafter proceed with the procedure of obtaining the biological sample under standard professional medical conditions (in cooperation with the "best practices" discussed herein. Upon obtaining the biological sample, the physician (and assisting staff) will reassemble the collection system by placing all the materials inside the system, seal with packing tape, and affix the return shipping label to the box. The physician will log into the business entities website, specifically, the physician portal, and fill in the prompts and schedule a "pick up" (most commonly by a commercial carrier) for returning to the processing facility.

The pre-determined fee for a physician to obtain the biological sample could vary but will mostly likely be limited to costs relating to the collection system and transportation to the processing facility. However, the cost will be a one-time set fee which will be agreed upon by the before initiating the procedure to obtain the sample.

The collection system is a defined set of components which are designed for coordination of the business method and identification material for the obtained biological sample. This is most commonly a defined group of standard forms which may include coded labels for use with an encoded program (as discussed herein).

Client sample bags included in the collection system have complimentary coded labels for use with the encoded program. These labels will comply with state and federal regulations, e.g. 21 CFR 11. The bags most commonly contain at least 35 and preferably 50 cubic centimeters ("cc") of a medium of human serum and are free of bovine albumin and free of any bovine serum (or other animal serum). The bags can be commercially obtained, for example, FlexBoy® Bioprocessing Bags. One skilled in the art would recognize the medium could include an antibiotic, e.g. Gentamicin, to address contamination issues. Further, the medium is essentially a basal medium containing only defined components which will support the survival of the cells of the biological sample.

Those skilled in the art would recognize the adjustment of the amounts of medium used, size of the bag, sample size obtained and disassociation reagents or devices will vary depending upon the amount of isolated material obtained. However, these variations are not contrary or "outside" of the business method of the present invention; the amounts used should be appreciated and recognized to define the proportional relationship of the components and that this "proportional relationship" is an important concept of the present embodiment and all other embodiments of the present invention in any form.

The collection system further includes a transportation box which may be commercially manufactured and coordinated with a transportation carrier, e.g. Biologics Box by FedEx. Transportation labeling will also include the complimentary coded labels for use with the same encoded program; in addition to information regarding shipment location. Upon coordination, the method continues by obtaining the biological sample from the client (via extraction by the physician/provider) and transporting the biological sample in the collection system to a processing facility. The process facility is automatically notified of each collection via the web-based system of the database to allow for receipt and preparation of material for processing.

At the processing facility, the collection system components are introduced to a processing module of the database via a log-in port; having the encoded program. The database will be custom-designed to process and store "e-protected" health information using commercially available programs such as Microsoft's Access program, Microsoft Sequel (SQL) and Oracle Database to optimize efficiency. The database will include but is not limited to, the information obtained from the collection system to coordinate the "client sample with the client"; such as the information included in the patient-specific bar-coded client sample bags. This information will also be included in a standardized form. The database will be organized in modules similar to the organization in the standardized form, will be searchable, and will be programmed to produce all the various forms associated with this business method. The database includes the encoded program to organize and store information regarding the biological sample and recording information.

As discussed herein, the database program is customized to the specific requirements for the coordination of biological sample to the client. The database will receive all data, including but not limited to storage, identification and distribution. Most commonly, the database(s) are encrypted using 256 bit encryption, with a six (6) character encryption key, and required user name and password entry for specific processes. Each entry is date and time stamped in addition to the user name which is stored locally for error tracking and Quality Control.

The biological sample is processed through disassociation (also referred to as "digestion") to separate and isolate material for cryopreservation. Prior to digestion, one of skill in the art would recognize that the obtained sample can be "washed" with an antibiotic, such as Gentamicin, so as to address contamination of the sample during collection. Any antibiotic will be reviewed in cooperation with the client information obtained during coordination of collection and the collection system so as to ensure that the client has no allergic reaction to the specific antibiotic used.

Disassociation can be by various means including, enzymatic and mechanical. A preferred example of enzymatic digestion includes a combination of collagenase and a neutral protease such as that found in Roche's Liberase®; this type of disassociation allows predictable yield amounts and cell viability. Mechanical disassociation methods may include Lipivage® (Genesis Biosystems); this type of disassociation allows reduced time and ease in obtaining the biological sample. Isolating the biological sample and ensuring the quality of the biological sample is an imperative key to the commercials success of the business method.

The business method includes separating from the isolated material at least three (3) test samples into vials for quality and viability testing. Testing is performed for quality control of the isolated material for cryopreservation and thereafter, the isolated material is cryopreserved in a first portable storage facility. The first of the at least three (3) vials is used in the testing after processing/disassociation and prior to cryopreservation. Based on this testing, a "Certificate of Analysis" is prepared which defines the isolated material, including but not limited to, method of disassociation, contaminates, size and the amount of cells in the isolated sample. The Certificate of Analysis will be distributed as directed by the client when requested and use of the isolated material is contemplated. The Certificate of Analysis is most commonly issued after a cryopreserved quality control aliquot is recovered and tested for both viability and contamination.

The first portable storage facility will include a stainless steel liquid nitrogen Dewar ("tank") with automated liquid nitrogen filling system and alarm. This defined tank will ensure a proper storage environment is maintained during "power outages" or other power disruptions.

The business method continues by selecting "outside" (e.g. separate from the first portable storage facility) facilities for storage of the isolated cryopreserved material. Most commonly, the outside storage facilities contemplate long term storage needs. These facilities are required to be certified cryopreservation facilities complying with all local, state and federal laws, and have the ability to handle clinical grade material. Further, these facilities will be able to supply and fulfill the volume needs of the samples to be preserved from a defined location. Most importantly, the facilities, selected or created, will coordinate the collection of the first portable storage facility, e.g. "freezers", from the processing facility. These outside facilities, such as Novara® Bio-Logistics, will most commonly form strategic partnerships within the business method of the current invention as second storage facility, which will maintain the cryopreserved isolated material.

The calculating of storage fees occurs for distributing of the isolated material to at least one of (i) client from which biological sample was obtained, (ii) research group or (iii) entity from which biological sample was not obtained. As appreciated by the business method of the previous embodiment, the client may "check off" a box on a standard form (completed during the collecting of the fee or coordinating collection of the biological sample) wherein they can sell/donate up to 20% of their sample as a clinical grade research specimen. This can be used as a cash return or as a discount on the storage of the sample. An average client sample is about 10 ml to 500 ml; allowing 20% of this sample to be applied to the storage costs which could translate into about 5 to 30 years of storage. The amount would vary but it is understood that the present method allows for this investment to "off-set" costs in order to obtain and sustain this valuable medical material.

The business method further includes (i) distributing the cryopreserved isolated material as directed by a client; and (ii) distributing one (1) of the at least three (3) test samples to the processing facility (or other designated testing facility) for quality control testing to confirm viability of the cryopreserved isolated material distributed as directed by a client. More specifically, the client's isolated material is sent via commercial carrier from the permanent storage facility as directed by the client; simultaneously, a test sample (stored with the isolated sample at the permanent storage facility) is sent via the same commercial carrier (with identical transport instruction to the processing facility (or other designated testing facility) for testing. Sending the test sample contemporaneously with the isolated material, as directed by the client, will ensure the viability of the client's isolated material is accurate and known by the business entity for quality control and quality assurance.

Most commonly, the obtained biological sample is an adipose tissue sample, wherein the product of the method is an isolated material in the form of a stromal vascular fraction ("SVF"), also referred to as stem cell "pellet" or SVF pellet, consisting essentially of a mixture of pre-adipocytes, adipose-derived mesenchymal stein cells, microvascular endothelial cells, endothelial progenitor cells, and monocytes. The isolated material will contain less than one (1) percent of any residual amount of any antibiotic used in the medium or "wash". Depending on the disassociation technique used; this amount could be undetectable.

The business method is adapted to process at least 35 and preferably at least 50 ccs of the adipose tissue into a SVF of at least 1.5 million cells, wherein at least 50% (percent) of the stromal vascular fraction of at least 1.5 million cells is viable. The business method described herein, produces each cell of the SVF pellet of at least 1.5 million cells are between 6.0 and 15.0 microns. As previously discussed, the variations within the ranges defined are based on the possible variations in the materials and methods but do effect the core concept of recognizing proportions and the interactive components of the business method or present invention In another embodiment the invention is directed to a method for collection, processing, cryogenic storage and distribution of an "autologous stem cell biological sample material derived from adipose tissue". The method is initiated by collecting a premium for defined services for collection, transportation, cryogenic storage and distribution of an autologous stem cell biological sample material derived from adipose tissue. As the method of the present embodiment is directed to an autologous procedure, e.g. the biological sample obtained from the client is the "core" material for the isolated material upon disassociation and processing, specific procedures are followed (as described herein) to ensure the autologous nature of the entire method/process.

Upon "enrollment" and collection of the premium the method continues by coordinating the collection of the autologous stem cell biological sample material derived from adipose tissue of a client including (i) paying a predetermined fee in support of physician/practitioner services performed for collection of the biological sample (it should be recognized the predetermined fee is "in support" of physician services; the present invention does not include payments for any medical procedures or services) and (ii) supplying a collection system including a plurality of components for collection and transportation of the biological sample. As in the previous embodiment, the collection system is specifically designed to reduce the probability of obtaining a sample that will be considered contaminated.

A practitioner obtains the autologous stem cell biological sample material derived from adipose tissue by various removal techniques from the client and transfers the autologous stem cell biological sample material derived from adipose tissue to a defined container having at least one port. The defined container will be included in the collection system. The collection system will include "best practices" information to obtain an uncontaminated sample and instructions for transporting the autologous stem cell biological sample material derived from adipose tissue in the collection system to a processing facility.

At the processing facility, technicians introduce the information from the collection system components to a processing module of a customized database. As with the previous embodiment, the database is specifically designed to enable inclusion of software to store and analyze information in a manner which adheres to good manufacturing practices ("GMP") and ensures privacy and accuracy of the patient samples.

Processing of the autologous stem cell biological sample material derived from the adipose tissue obtained by the practitioner occurs by disassociation to separate and isolate material for cryopreservation as described in the previous embodiment. At this point in the method, testing for quality control of the autologous isolated material for cryopreservation is performed and analysis of the results are reviewed and included in the database. Results of the testing will be given to the client for discussion and planning on how to proceed based on factors including contamination. A Certificate of Analysis (as discussed in the previous embodiment) can be included in any analysis for review by the client to make a decision regarding continuing the method to cryopreservation and use thereafter.

The autologous isolated material is cryopreserved as defined in the previous embodiment; one skilled in the art will recognize that cryopreservation rates, temperature etc. will not vary based on autologous versus homologous or heterologous samples obtained. However, recording and identification of the samples, via information in the database and standard operating procedure to identify samples will be implemented so as to ensure client privacy and identification of the isolated material. As with the previous embodiment, if an antibiotic is used in the collection or processing of the biological sample, the isolated material has less than one (1) percent of any antibiotic and potentially is devoid of any antibiotic or has undetectable amounts.

Selecting facilities for storage of the autologous isolated cryopreserved materials and storing the cryopreserved autologous isolated material in the selected facility will be performed based on the same criteria as the previous embodiment. Upon cryopreservation, storage fee will be calculated for distributing the cryopreserved isolated material designated by a client. The autologous isolated material is a SVF, again also referred to as stem cell "pellet" or SVF pellet, consisting essentially of a mixture of pre-adipocytes, adipose-derived mesenchymal stem cells, microvascular endothelial cells, endothelial progenitor cells, and monocytes which forms the product produced by the method and use by the client.

As with the previous embodiment, the method is adapted to process at least 35 and preferably 50 cc of the adipose tissue into a SVF pellet of at least 1.5 million cells, wherein at least 50% of the SVF pellet of at least 1.5 million cells is viable. The method described herein produces an SVF pellet, wherein each of the at least 1.5 million cells, are between 6.0 and 15.0 microns.

Referring to FIG. 1, in another embodiment, the invention is directed to a system for collection, cryogenic storage and distribution of a biological sample 10. The system 10 includes a collection system 12 and a collection system transportation system 14 to a processing facility 16, having access to a database 18. The database 18 includes an encoded program 20 to organize and store information regarding the biological sample and recording information. This includes information on standardized forms 22 which can be used in various parts of the system 10.

The collection system 12 has been defined in the previous embodiment and is usually in a "fitted box" for ease in use. As discussed herein, the collection system transportation system 14 is usually in coordination with a commercial carrier, such as Fed Ex®, which has the ability to transport medical samples using specific equipment in compliance with local, state and federal regulations.

At the completion of the processing at the processing facility 16, the isolated material is located in a first portable storage facility 24 as described herein, having the capability and construction to coordinate with a second (permanent) storage facility 26 such as Novara® Bio-Logistics. The liquid nitrogen in the first portable storage facility 24 and the second storage facility must maintain a temperature of less than −150 Celsius and preferably between −180 and −190 Celsius. Most commonly a strategic partnership is formed within the business method of the current invention. The first portable storage facility 24 "or freezer" is retrieved from the processing facility 16 and transported to a second storage facility 26, e.g. a Novara® Bio-Logistics facility via a first portable storage facility transportation system 28. The first storage facility transportation system 28 may include machinery which can move the first portable storage facility 24 with limited or no manpower so as to reduce or eliminate any potential damage to the first portable storage facility 24 or the isolated material therein.

At the occurrence of storage subscription renewal or a request for the cryogenically stored isolated material, a retrieval system 30 for calculating storage fees for distributing the isolated material to at least one of (i) client from which biological sample was obtained, (ii) research group;

(iii) entity from which biological sample was not obtained is used. Most commonly, the initial fees obtained are limited to the collection, disassociation and initial storage of the biological sample. This usually completes the first year of the relationship based on the fees and thereafter, a renewal period is required. Clients will then be required to "re-subscribe" for future storage that may or may not incorporate the "investment" option, as discussed, wherein a portion of their sample is invested as a research sample to "off-set" future storage costs. In general, clients must decide whether to incorporate the investment option prior to cryopreservation due to the requirement of quality control samples ("aliquots"). It is understood that various distinct applications of the "investment" concept may exist with the understanding of the general concept that a portion of the biological sample can be invested in return for cash or for additional storage time at the second storage facility.

Figure 2:
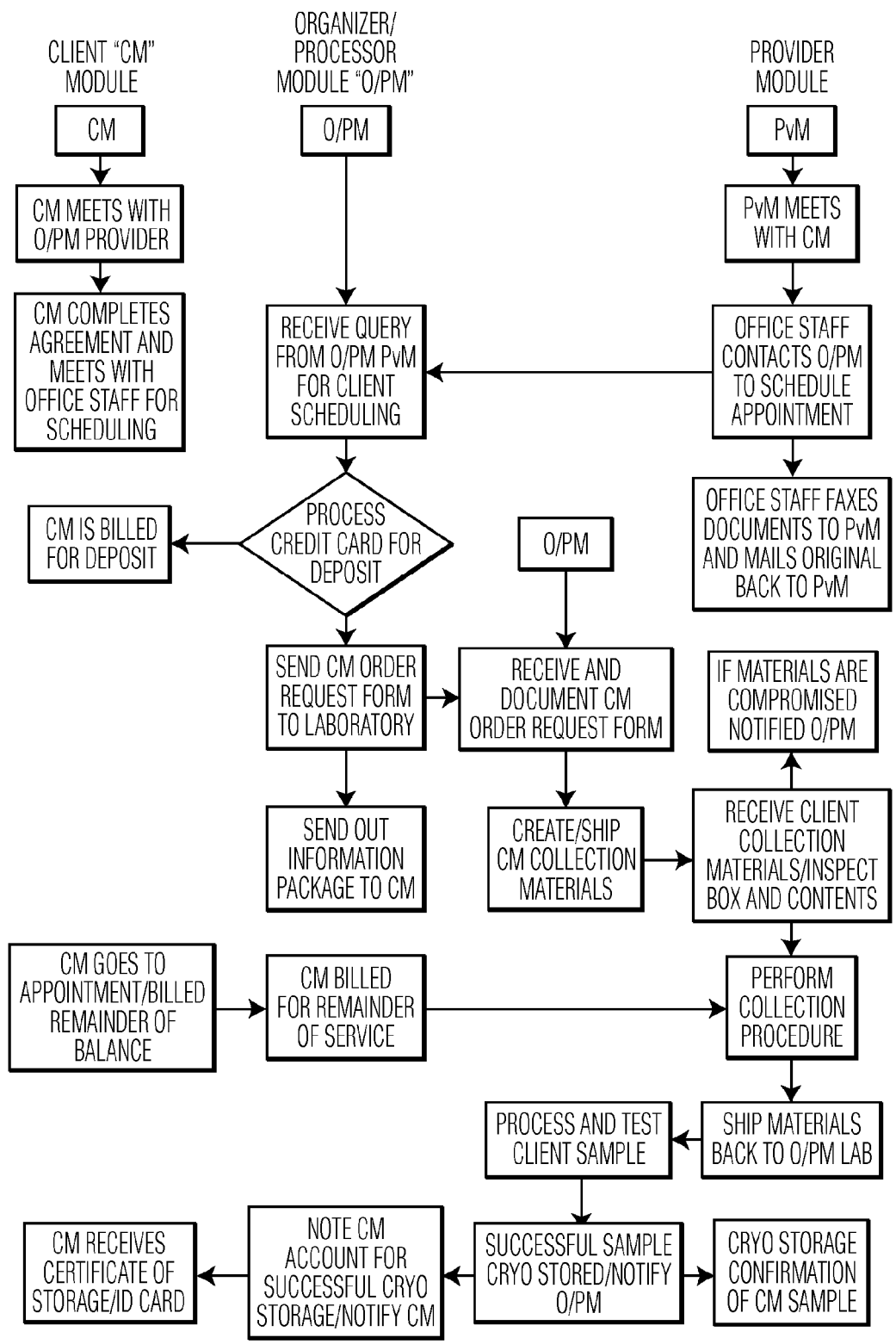
FIG. 2 is a schematic illustration of the interactive system of the present invention illustrating the interactive modules.

Referring to FIG. 2, an interactive system for collection, cryogenic storage and distribution of a biological sample is illustrated based on at least three interactive modules. The Organization or Processing Module ("O/P-M") is able to organize collection and storage of information from a Client Module ("CM"), most commonly a patient for obtaining and processing a biological material. A Provider Module ("PvM"), medical practitioner or other service provider, is capable to extract the biological material and initiate transport of the extracted biological sample to the first processing module for processing. The O/P-M includes computer executable logic capability for storing and analyzing information from the interactive modules based on a plurality of standard operating procedures for all processes and equipment used in the system and method. In addition, the O/P-M includes the capability to digest the biological sample obtained to form an isolated material (e.g. product) and thereafter cryopreserve the product for use as directed by CM.

The interactive system of the present embodiment can include all of the system and method components discussed herein in the previous embodiments (but not illustrated in FIG. 2) so as to accomplish the isolated material/product whether of an autologous, homologous or heterologous nature.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

The invention claimed is:

1. A method for collection, processing, cryogenic storage and distribution of a biological sample material comprising the steps of:
   a. coordinating the collection of a biological sample of a client comprising supplying a collection system comprising a plurality of components for collection and transportation of the biological sample;
   b. obtaining the biological sample from a client by standard medical practice removal techniques;
   c. transporting the biological sample in the collection system to a processing facility wherein the collections system comprises (a) identification material for the obtained biological sample (b) coded labels for use with an encoded program, (c) client sample bags, (d) transportation box and (e) transportation labeling;
   d. introducing information from the collection system to a processing module of a database having an encoded program, wherein the encoded program of the database is capable to automatically route new or changing information introduced into the database;
   e. processing the biological sample, wherein the biological sample is disassociated to separate and isolate material for cryopreservation by enzymatic digestion;
   f. testing for quality control of the isolated material for cryopreservation;
   g. cryopreserving the isolated material in a freezing apparatus;
   h. selecting outside facilities for storage of the isolated cryopreserved material;
   i. storing the cryopreserved isolated material in a liquid nitrogen tank having the ability to have alternate power sources; and
   k. separating from the isolated material at least three (3) test samples into vials after step (f) for quality and viability testing;
   l. preparing a certificate of analysis based on the testing in step f;
   m. (i) distributing the cryopreserved isolated material as directed by a client; and (ii) distributing (1) one of the at least three (3) test samples to a processing facility for quality control testing upon receipt at the processing facility to confirm viability of the cryopreserved isolated material distributed as directed by a client after step j;
   wherein the client sample bags include a medium comprising human serum which is free of animal albumin and animal serum which will support the survival of the cells of the biological sample;
   wherein the biological sample is washed with an antibiotic during processing;
   wherein the collection system components are introduced to a processing module of the database via a log-in port, by scanning a barcode on the client sample bag;
   wherein the obtained biological sample is an adipose tissue sample;
   wherein the isolated material is a stromal vascular fraction consisting essentially of a mixture of pre-adipocytes, adipose-derived mesenchymal stem cells, microvascular endothelial cells, endothelial progenitor cells, and monocytes having less than one (1) percent antibiotic;
   wherein the business method is adapted to process at least 35 cubic centimeters of the adipose tissue into the stromal vascular fraction of at least 1.5 million cells;
   wherein at least 50 percent of the stromal vascular fraction of at least 1.5 million cells are viable; and
   wherein each cell of the stromal vascular fraction of at least 1.5 million cells are between 6.0 and 15.0 microns.

2. The method of claim 1, wherein distributing the isolated material is to at least one of (i) client from which biological sample was obtained, (ii) research group or (iii) entity from which biological sample was not obtained.

3. A method for collection, processing, cryogenic storage and distribution of an autologous stem cell biological sample material derived from adipose tissue comprising the steps of:
   a. coordinating the collection of the autologous stem cell biological sample material derived from adipose tissue of a client comprising supplying a collection system comprising a plurality of components for collection and transportation of the biological sample;
   b. obtaining an autologous stem cell biological sample material derived from adipose tissue from a client;
   c. transferring the autologous stem cell biological sample material derived from adipose tissue to a defined container having at least one port, wherein the container contains a medium comprising human serum which is free of animal albumin and animal serum which will support the survival of the cells of the biological sample;

d. transporting the autologous stem cell biological sample material derived from adipose tissue in the collection system to a processing facility;

e. introducing information from the collection system components to a processing module of a customized database having an encoded program, wherein the encoded program of the database is capable to automatically route new or changing information introduced into the database;

f. processing the autologous stem cell biological sample material derived from adipose tissue, wherein the autologous stem cell biological sample material derived from adipose tissue is disassociated to separate and isolate material for cryopreservation;

g. testing for quality control of the autologous isolated material for cryopreservation;

h. cryopreserving the autologous isolated material in a freezing device;

i. selecting facilities for storage of the autologous isolated cryopreserved material;

j. storing the cryopreserved autologous isolated material in the selected facility in a liquid nitrogen tank having the ability to have alternate power sources; and k. distributing the cryopreserved isolated material designated by a client;

wherein the autologous isolated material is a stromal vascular fraction consisting essentially of a mixture of pre-adipocytes, adipose-derived mesenchymal stem cells, microvascular endothelial cells, endothelial progenitor cells, and monocytes;

wherein the method is adapted to process at least 35 cubic centimeters of the adipose tissue into a stromal vascular fraction of at least 1.5 million cells;

wherein steps b. through j. are under Good Manufacturing Practices;

wherein the autologous isolated material has not contacted non-human serum;

wherein at least 50 percent of the stromal vascular fraction of at least 1.5 million cells are viable;

wherein each cell of the stromal vascular fraction of at least 1.5 million cells are between 6.0 and 15.0 microns.

4. The method of claim 1, wherein disassociation by enzymatic digestion comprises a combination of collagenase and neutral protease to define yield amounts and cell viability.

* * * * *